US00PP19443P2

(12) United States Plant Patent
Jepsen

(10) Patent No.: US PP19,443 P2
(45) Date of Patent: Nov. 11, 2008

(54) ***KALANCHOE* PLANT NAMED 'LEA'**

(50) Latin Name: *Kalanchoe hybrida*
Varietal Denomination: Lea

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 60 days.

(21) Appl. No.: 11/454,064

(22) Filed: Jun. 15, 2006

(51) Int. Cl.
*A01H 5/00* (2006.01)

(52) U.S. Cl. ..... Plt./338

(58) Field of Classification Search ..... Plt./338, Plt./335

See application file for complete search history.

*Primary Examiner*—Kent L Bell
(74) *Attorney, Agent, or Firm*—C. A. Whealy

(57) ABSTRACT

A new and distinct cultivar of *Kalanchoe* plant named 'Lea', characterized by its upright, uniform and moderately vigorous growth habit; dark green-colored leaves; uniform, freely and early flowering habit; large double golden yellow-colored flowers; and excellent postproduction longevity.

1 Drawing Sheet

Botanical designation: *Kalanchoe hybrida.*
Cultivar denomination: 'Lea'.

BACKGROUND OF THE INVENTION

The present invention relates to a new and distinct cultivar of *Kalanchoe,* botanically known as *Kalanchoe hybrida,* and hereinafter referred to by the name 'Lea'.

The new *Kalanchoe* is a product of a planned breeding program conducted by the Inventor in Hinnerup, Denmark, The objective of the breeding program is to create new double-flowered *Kalanchoe* cultivars with attractive foliage and flower coloration.

The new *Kalanchoe* originated from a cross-pollination made by the Inventor in Hinnerup, Denmark in December, 2004, of the *Kalanchoe blossfeldiana*×*Kalanchoe laciniata* cultivar African Pearl, disclosed in U.S. Plant Pat. No. 17,973, as the female, or seed, parent with the *Kalanchoe blossfeldiana* cultivar Stella, not patented, as the male, or pollen, parent. The cultivar Lea was discovered and selected by the Inventor as a flowering plant from within the progeny of the stated cross-pollination in a controlled environment in Hinnerup, Denmark in August, 2005.

Asexual reproduction of the new *Kalanchoe* by vegetative terminal cuttings in a controlled environment in Hinnerup, Denmark since August, 2005, has shown that the unique features of this new *Kalanchoe* are stable and reproduced true to type in successive generations.

SUMMARY OF THE INVENTION

The cultivar Lea has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Lea'. These characteristics in combination distinguish 'Lea' as a new and distinct cultivar of *Kalanchoe:*

1. Upright, uniform and moderately vigorous growth habit.
2. Dark green-colored leaves.
3. Uniform, freely and early flowering habit.
4. Large double golden yellow-colored flowers.
5. Excellent postproduction longevity.

Plants of the new *Kalanchoe* can be compared to plants of the female parent, the cultivar African Pearl. Plants of the new *Kalanchoe* differ from plants of the cultivar African Pearl in the following characteristics:

1. Plants of the new *Kalanchoe* are more compact than plants of the cultivar African Pearl.
2. Plants of the new *Kalanchoe* and the cultivar African Pearl differ in leaf shape as plants of the cultivar African Pearl have hastate-shaped leaves.
3. Plants of the new *Kalanchoe* and the cultivar African Pearl differ in flower coloration.

Plants of the new *Kalanchoe* can be compared to plants of the male parent, the cultivar Stella. Plants of the new *Kalanchoe* differ from plants of the cultivar Stella in the following characteristics:

1. Plants of the new *Kalanchoe* and the cultivar Stella differ in leaf shape as plants of the cultivar Stella have ovate-shaped leaves.
2. Plants of the new *Kalanchoe* and the cultivar Stella differ in flower coloration.

Plants of the new *Kalanchoe* can be compared to plants of the *Kalanchoe blossfeldiana* cultivar Karen, not patented. In side-by-side comparisons conducted in Hinnerup, Denmark, plants of the new *Kalanchoe* differed from plants of the cultivar Karen in the following characteristics:

1. Plants of the new *Kalanchoe* were more compact than plants of the cultivar Karen.
2. Plants of the new *Kalanchoe* and the cultivar Karen differed in leaf shape as plants of the cultivar Karen had elliptic-shaped leaves.
3. Plants of the new *Kalanchoe* had larger inflorescences and larger flowers than plants of the cultivar Karen.
4. Flowers of plants of the new *Kalanchoe* had more petals than flowers of plants of the cultivar Karen.

5. Plants of the new *Kalanchoe* flowered about three days later than plants of the cultivar Karen.
6. Plants of the new *Kalanchoe* and the cultivar Karen differed in flower color.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.*

The photograph at the top of the sheet comprises a side perspective view of a typical flowering plant of 'Lea' grown in a container.

The photograph at the bottom of the sheet comprises a top perspective view of a typical flowering plant of 'Lea' grown in a container.

DETAILED BOTANICAL DESCRIPTION

The photographs and following observations, measurements and values describe plants grown in Hinnerup, Denmark in a glass-covered greenhouse during the winter and early spring and under conditions which closely approximate commercial production. During the production of the plants, day temperatures were about 19° C., night temperatures were about 21° C. and light levels ranged from 10 kilolux to 50 kilolux. Unrooted cuttings were directly stuck in 10-cm containers and received long day/short night conditions (more than 14 hours of light) for about two weeks; plants than received photoinductive short day/long night conditions (minimum 14 hours darkness) until flowering. Plants were about 16 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe hybrida* cultivar Lea.

Parentage:

*Female, or seed, parent.*—*Kalanchoe blossfeldiana*× *Kalanchoe laciniata* cultivar African Pearl, disclosed in U.S. Plant Pat. No. 17,973.

*Male or pollen parent.*—*Kalanchoe blossfeldiana* cultivar Stella, not patented.

Propagation:

*Type.*—By vegetative terminal cuttings.

*Time to initiate roots.*—About two to three weeks at temperatures of 19° C. to 21° C.

*Time to produce a rooted young plant.*—About 21 to 24 days at temperatures of 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit. Very freely flowering with numerous compound cymes. Inverted triangle with rounded crown. Appropriate for 6-cm to 10-cm containers.

*Plant height at flowering.*—About 20 cm.

*Plant diameter at flowering.*—About 22 cm.

*Branching habit.*—Usually about four to nine lateral branches develop per plant. Pinching (removal of the terminal apex) is not required but will enhance lateral branch development.

Lateral branch description:

*Length.*—About 13 cm.

*Diameter.*—About 4 mm.

*Internode length.*—About 1 cm to 2 cm.

*Aspect.*—Erect.

*Strength.*—Strong.

*Texture.*—Smooth, glabrous.

*Color.*—147B.

Foliage description:

*Arrangement.*—Opposite, simple; generally symmetrical.

*Length, vegetative plants.*—About 8 cm to 12 cm.

*Width, vegetative plants.*—About 6 cm to 8 cm.

*Length, generative plants.*—About 5 cm to 6 cm.

*Width, generative plants.*—About 5 cm.

*Shape.*—Ovate to orbicular.

*Apex.*—Obtuse.

*Base.*—Truncate.

*Margin.*—Crenate.

*Texture, upper and lower surfaces.*—Glabrous; leathery; succulent.

*Venation pattern.*—Pinnate.

*Color.*—Developing and fully developed foliage, upper surface: 147A; venation, 147A. Developing and fully developed foliage, lower surface: 147B; venation, 147B.

*Petiole.*—Length: About 2 cm to 3 cm. Diameter: About 5 mm to 7 mm. Texture, upper and lower surfaces: Smooth, glabrous. Color, upper surface: 137D. Color, lower surface: 137C.

Flower description:

*Flower arrangement and habit.*—Double flowers arranged singly in compound dichasial cymes that arise from leaf axils. Uniform and freely flowering habit with usually about 20 to 40 open flowers per inflorescence. Flowers not persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Early flowering habit; under short day/long night photoinductive conditions, about 71 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 10 cm to 12 cm.

*Inflorescence diameter.*—About 6 cm.

*Flower diameter.*—About 2.6 cm.

*Flower length (height).*—About 1.1 cm.

*Flower bud.*—Shape: Ellipsoidal. Length: About 1.5 cm. Diameter: About 3 mm. Color: 15C tinged with 30A.

*Petals.*—Arrangement: About 25 fused at the base. Lobe length (largest petals): About 1.3 cm. Width (largest petals): About 8 mm. Shape: Ovate. Apex: Mucronate. Margin: Entire. Texture, upper and lower surfaces: Smooth, glabrous. Color: When opening, upper surface: 21A. When opening, lower surface: 15C tinged with 30A. Fully opened, upper surface:

15A; color becoming closer to 15C with development. Fully opened, lower surface: 15C tinged with 30A.

*Sepals.*—Appearance: Four fused at the base. Length: About 1.1 cm. Width: About 2 mm. Shape: Lanceolate, linear. Apex: Acute. Margin: Entire. Texture, upper and lower surfaces: Smooth; glabrous. Color, immature, upper and lower surfaces: 144A. Color, mature, upper and lower surfaces: 144A.

*Peduncles.*—Length: About 2 cm. Diameter: About 3 mm. Aspect: Erect to about 60° from vertical. Strength: Strong. Texture: Smooth, glabrous. Color: 137C.

*Pedicels.*—Length: About 2 mm to 6 mm. Diameter: About 3 mm. Aspect: Erect to about 90° from vertical. Strength: Strong. Texture: Smooth, glabrous. Color: 137C.

*Reproductive organs.*—Androecium: Stamen number: About five to ten per flower. Anther shape: Elliptic. Anther size: About 1 mm by 1 mm. Anther color: 22A. Amount of pollen: Scarce. Pollen color: 20A. Gynoecium: Pistil number: About four per flower. Pistil length: About 3 mm. Style length: About 2 mm. Style color: 145A. Stigma shape: Rounded. Stigma color: 145A. Ovary color: Close to 138A.

*Seed.*—Length: About 1 mm. Diameter: About 0.5 mm. Color, immature: 145C. Color, mature: 177A.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Lea' as illustrated and described.

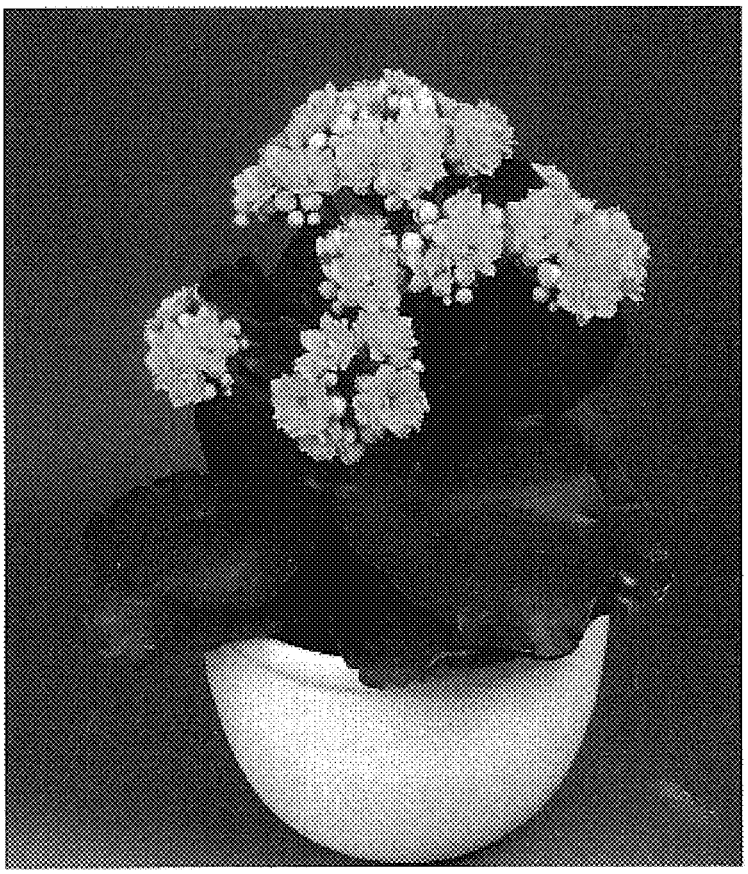
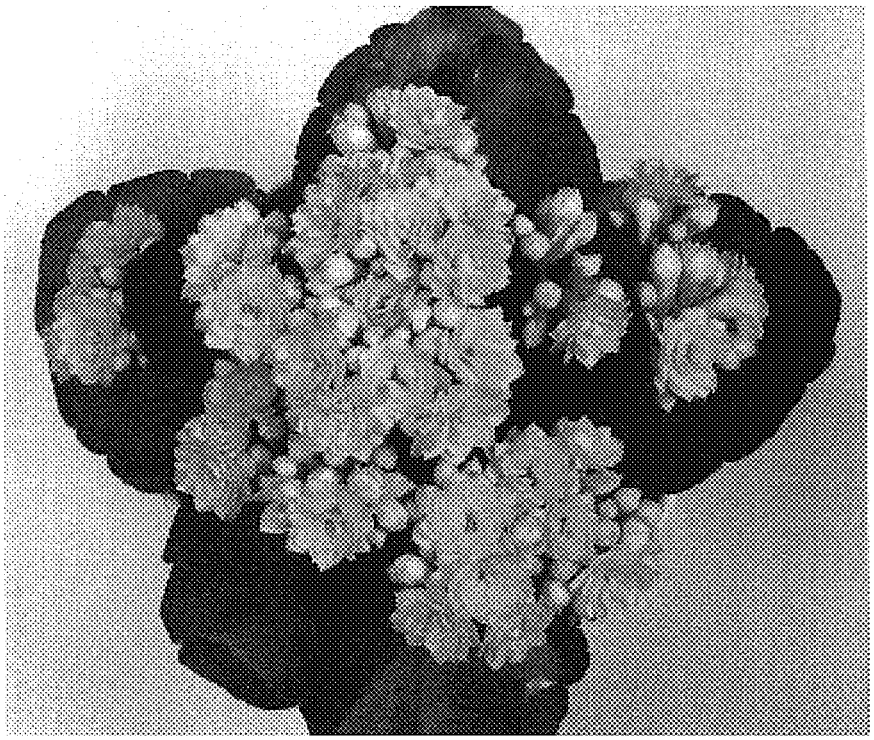

* * * * *